US005702458A

United States Patent [19]
Burstein et al.

[11] Patent Number: 5,702,458
[45] Date of Patent: Dec. 30, 1997

[54] JOINT PROSTHESIS

[75] Inventors: Albert H. Burstein, Longboat Key, Fla.; Donald L. Bartel, Freeville, N.Y.

[73] Assignee: New York Society for The Ruptured and Crippled Maintaining The Hospital for Special Surgery, New York, N.Y.

[21] Appl. No.: 383,757

[22] Filed: Feb. 2, 1995

Related U.S. Application Data

[63] Continuation of Ser. No. 352,898, Dec. 9, 1994, abandoned.

[51] Int. Cl.⁶ ............................................. A61F 2/38
[52] U.S. Cl. ................................................. 623/20
[58] Field of Search ................................. 623/18, 20

[56]   References Cited

U.S. PATENT DOCUMENTS

| 4,213,209 | 7/1980 | Insall et al. | 623/20 |
| 4,298,992 | 11/1981 | Burstein et al. | 623/20 |
| 4,892,547 | 1/1990 | Brown | 623/20 |
| 5,011,496 | 4/1991 | Fortz et al. | 623/20 |
| 5,147,405 | 9/1992 | Vanzile et al. | 623/20 |
| 5,370,699 | 12/1994 | Hood et al. | 623/20 |

*Primary Examiner*—David Isabella
*Attorney, Agent, or Firm*—Darby & Darby

[57]   ABSTRACT

A knee joint prosthesis comprises femoral and tibial components. The femoral component includes a pair of condyles each curved generally to match the shape of an anatomical femoral condyle. The surface of each condyle is defined by (a) anterior posterior radii $R_{CF}$ and $R_{CE}$, wherein $R_{CF}$ is the radius of curvature Of that portion of the condyle which is weight bearing in flexion and $R_{CE}$ represents that portion of the curvature of the condyle which is weight bearing in extension, and (b) a medial lateral radius $R_{CML}$. The tibial component includes a pair of concavities, each of which is adapted to receive one of the condyles of the femoral component. The surfaces of the concavities are defined by an anterior posterior radius $R_{TAP}$ and a medial lateral radius $R_{TML}$. The foregoing radii are selected to optimize the balance between range of motion and knee longevity.

5 Claims, 3 Drawing Sheets

JOINT PROSTHESIS

This is a continuation of application Ser. No. 08/352,898, filed Dec. 9, 1994, now abandoned.

This invention relates to joint prostheses such as total knee prostheses of the type intended to replace all surfaces of the femur and tibia which engage each other at the knee joint.

BACKGROUND OF THE INVENTION

Artificial joint prostheses are commonly used today for many different joints in the human body. One such common prosthesis is known as a total knee prosthesis. Virtually all total knee prostheses comprise a metallic femoral component and a tibial component which includes a plastic platform. The femoral component includes spaced apart condyles shaped generally to match the anatomical femoral condyles. The femoral condyles are received in spaced apart concavities within the tibial platform, with the shape of the condyles and concavities being selected so that a range of motion of approximately 130° in flexion to approximately 8° hyperextension is available.

U.S. Pat. No. 4,298,992 of Burstein and Insall discloses a posteriorly stabilized total knee joint prosthesis which has gained widespread acceptance as the Insall Burstein knee. The Insall Burstein knee comprises femoral and tibial components which permit relative motions closely resembling those of the anatomical joint it replaces, Such motions include flexion, anterior-posterior translation, lateral angulation and axial rotation. The Insall Burstein knee is posterially stabilized by the interaction of a tibial post and cam-follower portion on the femoral component which, .during flexion, prevents excessive posterior movement of the tibia relative to the femur.

Burstein et al. U.S. Pat. No. 4,298,992 is hereby incorporated herein by reference.

In addition to knees, there are other types of prostheses in which a pair of condyles are received in spaced apart concavities to replicate a human anatomical joint. For example, bicondylar prostheses are used for ankles and fingers. The present invention is applicable to any artificial prosthesis in which a pair of condyles are received in complementary concavities. Because the invention has been embodied in a knee, the principles of the invention are described in connection with a total knee prosthesis for purposes of explanation. In the following explanation, reference is made specifically to a posterior stabilized total knee prosthesis in which posterior dislocation of the tibia relative to the femur is prevented during flexion by engagement of a femoral cam follower surface with a tibial post. Insofar as a knee prosthesis is concerned, the principles of the invention are equally applicable to a total condylar knee prosthesis of the posterior cruciate sparing type which does not contain a tibial post or femoral cam follower surface and which may or may not have a central notch in the tibial component to allow retention of the natural posterior cruciate ligament. Because of the similarity of these two knees, only one (posterior stabilized) is described in this specification.

The longevity of a total knee replacement is of obvious concern. The greater the stress at the contact surfaces between the femoral and tibial components, the greater the degradation of the surfaces, particularly the plastic tibial platform in which the femoral condyles are nested. In the Insall Burstein and similar knees, stress caused by the contact loads between the femoral and tibial surfaces can be reduced by increasing the conformity of the components. That is, if the radii of the convex femoral condyles are made larger to more closely match (conform to) the radii of the concavities in the tibial platform, Istress (and, therefore, long term degradation) will be minimized. However, when there is close conformity of the femoral and tibial components, the range of motion of the knee, especially flexion-extension and axial rotation, is limited and the tendency of the components to loosen is increased. Axial rotation is the amount of angular movement that occurs between the tibial and femoral components when they are simultaneously subject to axial compressive load and axial torsion in values encountered during normal gait activities. Thus, there is a tradeoff between contact stress under a compressive load (which is desirably minimized when the radii of curvature are totally conforming) and range of motion, particularly axial rotation, which is minimized when the contacting surfaces conform.

The present invention provides a bicondylar joint replacement, of the type including a bicondylar component which rests in a complementary platform, in which stresses on the platform under compressive load are substantially reduced without any loss of stability or range of motion. Accordingly, longevity of the joint is increased without sacrificing stability or range of motion.

The invention is particularly well suited for use in conjunction with a total knee replacement (such as the Insall-Burstein knee) either of the posterior-stabilized or cruciate-sparing type. In fact, the invention provides a total knee replacement which is improved as compared to the Insall Burstein knee in other respects as well. By changing the shape of the femoral condyles, tension in the soft tissues (i.e. ligaments) which attach to the medial and lateral sides of the patella is reduced. This reduces complications which can occur at the patella-femoral joint.

SUMMARY OF THE INVENTION

A bicondylar joint prosthesis comprises first and second components. The first (e.g. femoral) component includes a pair of laterally spaced apart condyles each of which is curved generally to match the shape of an anatomical condyle. The surface of each condyle is defined at least in part by (a) anterior posterior radii $R_{CF}$ and $R_{CF}$, where $R_{CF}$ represents the radius of curvature of that portion of the condyle which is weight bearing in flexion and $R_{CE}$ represents that portion of the curvature of the condyle which is weight bearing in extension, and (b) a medial lateral radius $R_{CML}$. The second (e.g. tibial) component includes a pair of laterally spaced apart concavities, each of which is adapted to receive one of the condyles of the first component. The surfaces of the concavities are defined by an anterior posterior radius $R_{TAP}$ and a medial lateral radius $R_{TML}$. The foregoing radii as expressed by the ratios $R_{CF}/R_{TAP}$, $R_{CE}/R_{TAP}$, and $R_{CML}/R_{TML}$ are selected so as to optimize the balance between range of motion, particularly rotation, and joint longevity.

The combination of the ratios of $R_{CML}/R_{TML}$ and $R_{CF}/R_{TAP}$ are selected to minimize the stresses caused by contact loads during both knee flexion and extension while at the same time allowing adequate axial rotation of the knee joint in its most restricted range of motion, i.e. during the tightest fit between tibia and femor in which contact is maintained on the condylar arc defined by $R_{CE}$. The ratio of $R_{CF}/R_{TAP}$ is independently chosen to provide the acceptable range of flexion-extension motion of approximately 130°.

IN THE DRAWINGS

DETAILED DESCRIPTION OF A PREFERRED EMBODIMENT

Figure 5:
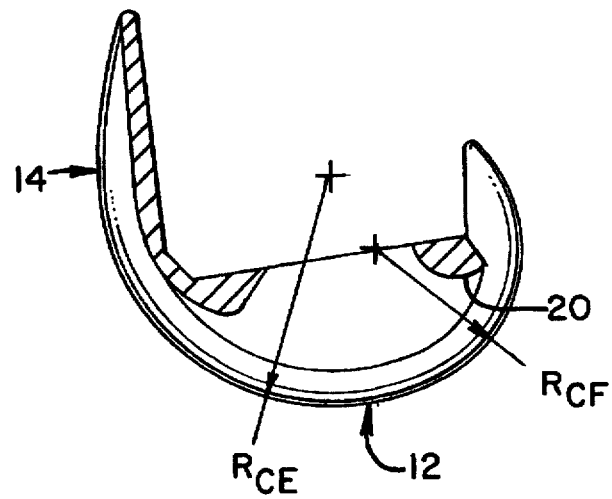
FIG. 5 is a sectional view along the line 5—5 of FIG. 4.
Figure 6:
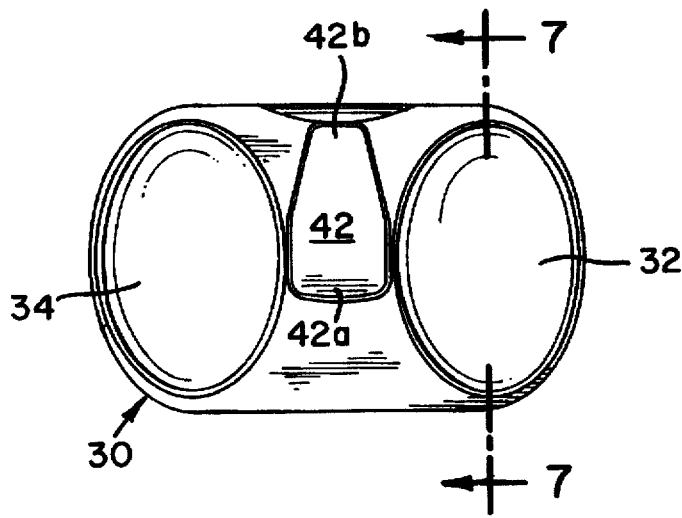
FIG. 6 is a top view of the tibial component.
Figure 7:
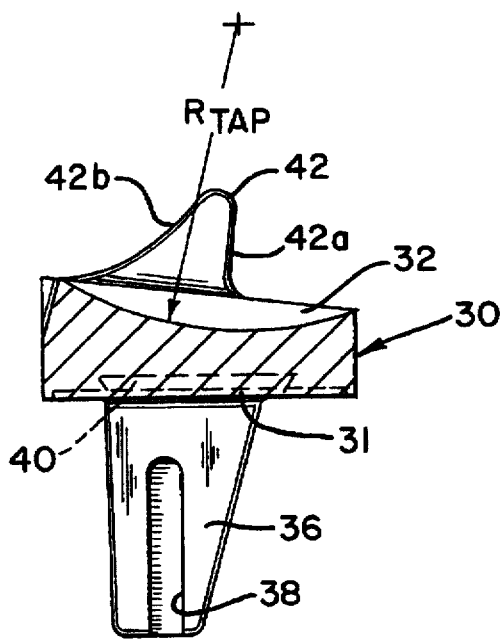
FIG. 7 is an anterior-posterior cross section of the tibial component along the line 7—7 of FIG. 6.
Figure 8:
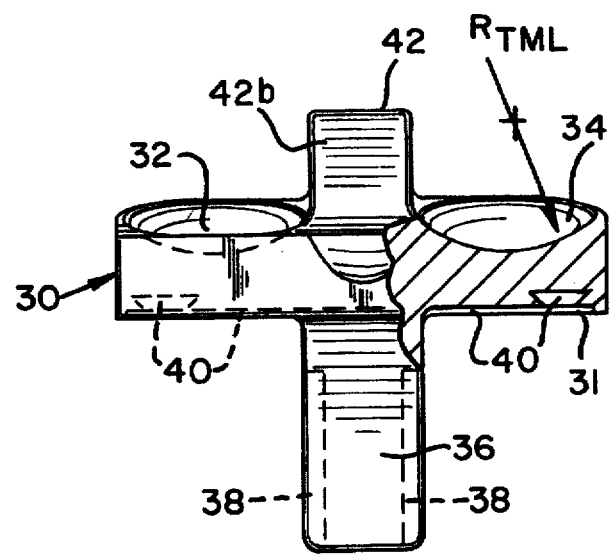
FIG. 8 is a posterior view of the tibial component partially in cross section.
Figure 9:
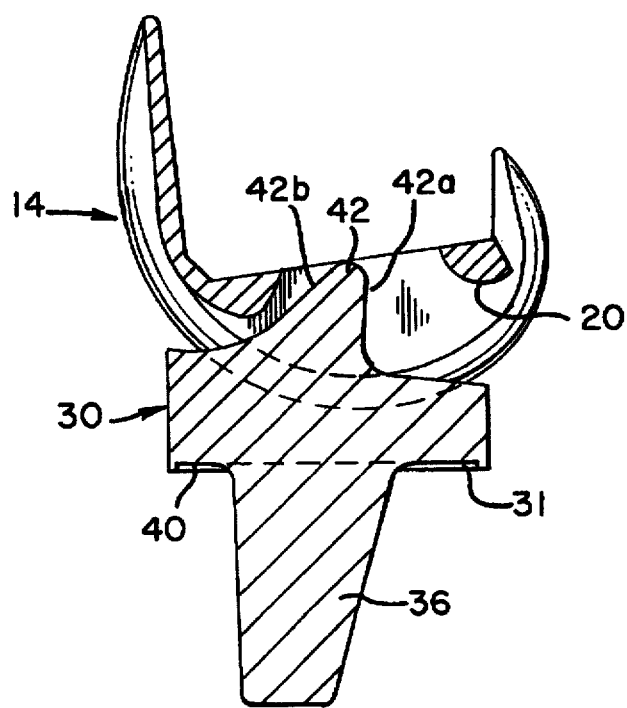
FIG. 9 is a sectional view in the anterior-posterior plane showing the femoral component nested within the tibial component.

The drawings illustrate a posterior-stabilized total knee prosthesis including a femoral component (FIGS. 1–5) and a tibial component (FIGS. 6–8). The illustrated prosthesis is a modified form of the Insall-Burstein knee.

The femoral component comprises a pair of identical laterally spaced-apart femoral condyles 10 and 12, each of which is curved in lateral profile (FIG. 2) generally to match the convex curvature of an anatomical femoral condyle along its entire anterior-posterior extent. The anterior parts of the condyles merge smoothly with convexly curved portions 14a and 14b of a patellar flange 14, the middle part 14c of which is concave. The middle patellar part 14c intersects at its lower extremity an anterior wall 16a of a box-like intercondylar portion 16. The anterior wall 16a and a femoral cam follower 20 (described below) together with patellar portion 14, connect the condyles 10 and 12. A pair of laterally spaced-apart walls 16b and 16c join the patellar flange to the condyles and form the sides of the box-like intercondylar portion 16.

The surfaces of the femoral component which face the surgically prepared femur bone are generally flat and, in the case of the "facets" of each condyle 10 and 12, are bounded by a small rib or flange 19 (FIG. 1) to provide a keying effect which holds the component securely on the cement used to attach the component to the femur.

The upper surface of the anterior wall 16a of the intercondylar portion 16 is generally flat. It slopes upwardly from its anterior surface toward a cam follower 20 at the posterior extremity of intercondylar portion 16, and includes a generally square opening 18.

The femoral component is preferably made of a surgical grade, durable metal, such as a 316L stainless steel or a chrome-cobalt-molybdenum alloy or ceramic material such as alumina or zirconia. All surfaces which are external to the bone are highly polished. The femoral component is symmetrical about a vertical anterior-posterior center plane, so it can be used on either knee.

The tibial component is shown in FIGS. 6–8 at 30. It may be made entirely of plastic (as shown) or it may include a plastic insert mounted on a metal tray. It is preferably made of a surgical grade, low friction, high molecular weight polyethylene. It is symmetrical about a vertical anterior-posterior center plane for right or left use. The upper surface of platform 30 slopes downwardly in the posterior direction. Two laterally spaced-apart, oblong concavities 32 and 34 are formed in the upper surface of plateau portion 30 to receive the femoral condyles 12 and 10, respectively. The "nested" support of the femoral component stabilizes the prosthetic joint but still permits anterior-posterior translation, lateral angularion and axial rotation, all of which are involved in normal function of the anatomical knee joint. The lateral curvature of concavities 32 and 34 is slightly greater than the lateral curvature of the femoral condyles 10 and 12.

A fixation post 36 extends from the bottom surface 31 of component 30. Cement intrudes into slots 38 in the walls of the fixation post and slots 40 on the bottom surface of the support and anchors the tibial component to the tibia.

A stabilizing post 42 extends upwardly from the plateau portion between the concavities 32 and 34 and is received in hole 18 of the femoral intercondylar portion 16. The post 42 is generally triangular in lateral profile and has lateral surfaces, a posterior surface 42a which functions as a cam and an anterior upwardly sloping surface 42b which functions as a hyperextension stop when contacting anterior wall 16a. The lateral surfaces of the stabilizing post 42 are spaced sufficiently from the lateral walls of the femoral intercondylar recess to allow normal lateral angularion and rotation of the prosthetic knee joint.

With the leg extended, a generally stable position is established by the nesting of the femoral condyles 10 and 12 in the tibial plateau concavities 34 and 32. The tibial stabilizing post 42 and femoral recess 16 do not engage in the anterior-posterior direction. Under moderate degrees of flexion the post and recess continue to remain functionally dormant. The femoral cam 20 tends to engage the posterior cam surface 42a of the tibial post 42 as the knee flexes. Somewhere around 70° to 80° flexion the femoral cam 20 should ordinarily engage the tibial cam surface 42a and, as flexion increases beyond that point, force the prosthetic femoral condyles to roll back in the tibial concavities. The zone of contact between the condyles and the concavities shifts posteriorly to a location very close to the posterior extremity of the tibial plateau at full flexion. This shift and the sloping of the tibial plateau allows large flexion angles to be obtained without interference between the posterior extremity of the femur and the posterior extremity of the tibial component. The post and recess thus stabilize joint functions near and at full flexion by controlling the relative anterior-posterior positions of the femur and the tibia and by preventing anterior femoral translation.

If the knee should undergo a fairly large hyperextension, say about 8°, the anterior part of the wall 16a of the femoral intercondylar portion 16 will engage the anterior surface of the tibial post 42b and prevent hyperextension and posterior translation of the femur.

In use, the femoral condyles 10 and 12 are nested in the tibial concavities 34 and 32. As indicated above, it is this relationship which is primarily responsible for knee stability, range of motion and durability. The proper selection of tibial concavity curvature and femoral condyle curvature in accordance with the invention is particularly effective in reducing stress applied to the tibial platform when the knee undergoes varus or valgus angulation when bearing load. When the curves of the condyles 10 and 12 conform closely to the curves of concavities 32 and 34, stress applied to the tibial platform is minimized under a compressive load; however, the range of motion, particularly axial rotation, is also reduced. In accordance with the invention, by slightly modifying the radii of the curves of the condyles and concavities the invention provides increased durability, i.e. longevity, without diminishing stability, range of motion or axial rotation.

Figure 1:
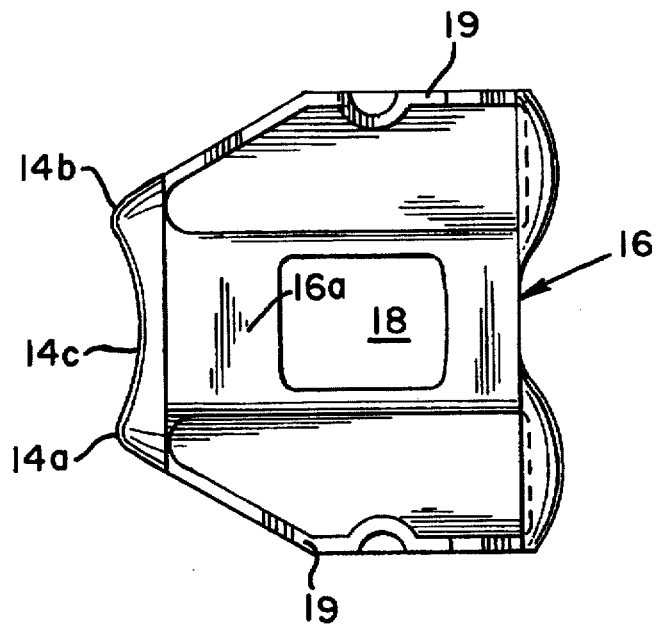
FIG. 1 is a top plan view of the femoral component of a knee prosthesis in accordance with the invention.
Figure 2:
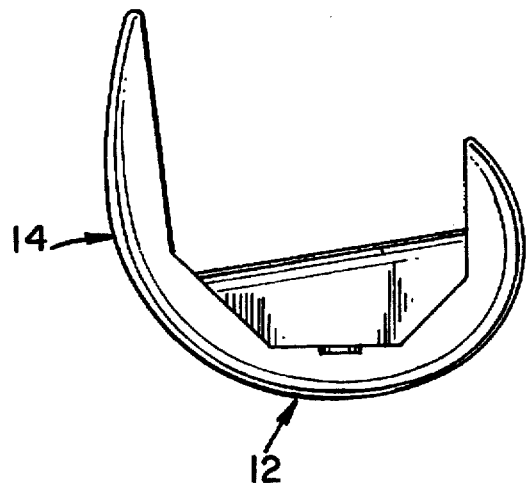
FIG. 2 is a side plan view of the femoral component.
Figure 3:
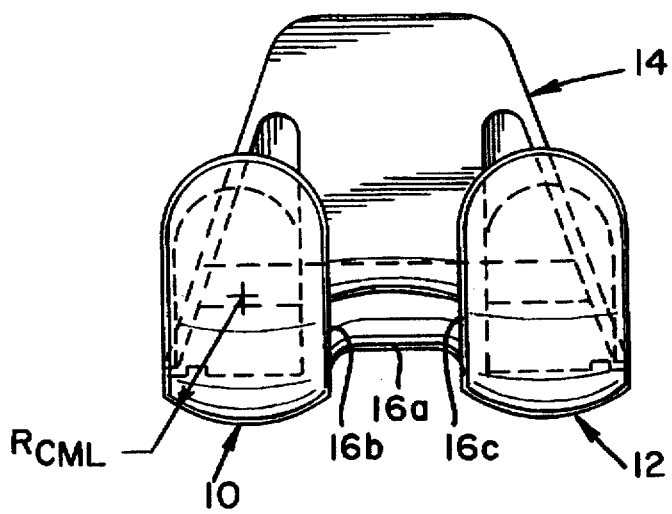
FIG. 3 is a rear (posterior) view of the femoral component.
Figure 4:
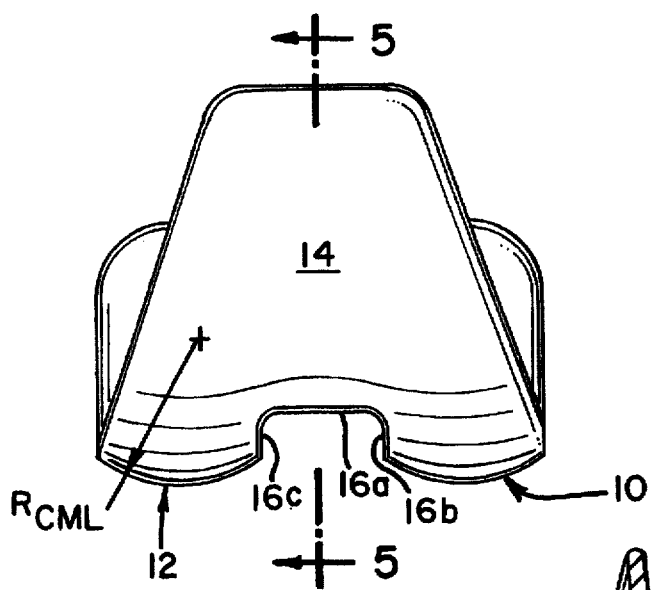
FIG. 4 is a front (anterior) view of the femoral component.

As shown in FIG. 3, the curve of the condyles 10 and 12 viewed in a lateral plain may be defined by a radius designated as $R_{CML}$. As shown in FIG. 5, the curvature of the weight bearing surfaces of the condyles as viewed in an anterior-posterior plane may be defined by the radii $R_{CE}$ and $R_{CF}$. The radius $R_{CE}$ defines the curvature of the surface of the condyle which rests in a tibial concavity when the knee is in extension. The radius $R_{CF}$ defines the curvature of the surface of the condyle that rests in a tibial concavity when the knee is in flexion.

The surface of the tibial concavities 32 and 34 are further defined by a medial-lateral radius $R_{TML}$ (FIG. 8) and anterior-posterior radius $R_{TAP}$ (FIG. 7).

The optimum radii which have been established pursuant to the invention may be expressed as the ratio of the radii of the femoral condyles to the corresponding radii of the tibial concavities in both the medial/lateral and anterior/posterior directions. Since the condyles are defined by two radii in the anterior/posterior direction, i.e. the radii $R_{CF}$ and $R_{CE}$ representing, respectively, the weight bearing portions of the curvature when the knee is in flexion and extension, the relationships between the components may be defined by the ratios $R_{CML}/R_{TML}$, $R_{CF}/R_{TAP}$ and $R_{CE}/R_{TAP}$. Moreover, since knee prostheses come in different sizes, the ratios are not necessarily the same for each available size. The illustrated embodiment of the invention is shown in five different sizes and the following tables set forth the approximate ratios in accordance with the invention for five different sizes with size 1 being the smallest and size 5 being the largest. The tables also include the corresponding radii for the prior art Insall Burstein knee identified as "I-B II".

TABLE I

| | $R_{CML}/R_{TML}$ | | $R_{CE}/R_{TAP}$ | |
|---|---|---|---|---|
| SIZE | I-B II | INVENTION | I-B II | INVENTION |
| 1 | 0.94 | 0.96 | 0.90 | 0.67 |
| 2 | 0.94 | 0.96 | 0.90 | 0.67 |
| 3 | 0.94 | 0.96 | 0.90 | 0.67 |
| 4 | 0.94 | 0.96 | 0.90 | 0.67 |
| 5 | 0.94 | 0.96 | 0.90 | 0.67 |

TABLE II

| | $R_{CF}/R_{TAP}$ | |
|---|---|---|
| SIZE | I-B II | INVENTION |
| 1 | 0.39 | 0.43 |
| 2 | 0.39 | 0.43 |
| 3 | 0.39 | 0.43 |
| 4 | 0.39 | 0.43 |
| 5 | 0.39 | 0.43 |

It is seen from Table I that the ratio $R_{CML}/R_{TML}$ is to be as close to the value of 1.00 as is obtainable consistent with obtaining adequate axial rotation when taken in combination with $R_{CE}/R_{TAP}$. The use of the value 1.00 for the ratio $R_{CML}/R_{TML}$ is not acceptable since this will overly restrict axial rotation. A value of $R_{CML}/R_{TML}$ of about 0.96 is preferred when used in combination with a value of $R_{CE}/R_{TAP}$ of about 0.60 to 0.75. Using the I-BII as a comparison, the contact-load-induced stresses on the tibial component in the illustrated embodiment will be reduced because of the increase of the ratio $R_{CML}/R_{TML}$ while at the same time the reduction of the ratio $R_{CE}/R_{TAP}$ will tend to increase these stresses. The combination of the two changes results in a net decrease in contact stresses without meaningful change in axial rotation of the knee joint.

It is seen from Table II that the ratio $R_{CF}/R_{TAP}$ is to be about 0.4 to 0.5. This value will independently contribute to lower contact-load-induced stresses as compared to the I-BII, while not decreasing axial rotation meaningfully. In combination with the preferred ratio of $R_{CML}/R_{TML}$, the indicated values of $R_{CF}/R_{TAP}$ produce greater axial rotation in the flexed position of the knee joint than that produced by the corresponding radii of curvature when the knee is in the extended position.

In addition to the foregoing, other improvements have been incorporated into the preferred embodiment as compared to the Insall Burstein II knee. For one, the radii $R_{CE}$ of the femoral condyles 10 and 12 have been substantially reduced. The effect is to remove bulk from the condyles and thereby reduce tension in the soft tissues that attach to the medial and lateral sides of the patella (not illustrated). This reduces complications which can occur at the patella-femoral joints, such as dislocation, subluxation (i.e. movement of the patella in and out of the trochlea grove), pain and even possible fracture of the patella.

Moreover, the height of the anterior portion of the femoral component has been increased. This enhances the ability of the knee to engage the patella when the knee is fully extended.

In addition, on the tibial component the tibial post 42 has been increased in height and the cam surface 42a moved in a posterior direction. The increased height of post 42 makes it more difficult for the femoral component to slip over the post. Repositioning the cam surface 42a allows an essentially uniform range of motion for all size prosthetic knee joints.

What is claimed is:

1. A joint prosthesis comprising:
   a first component which includes a pair of laterally spaced apart condyles, the surface of each said condyle being defined at least in part by (a) anterior posterior radii $R_{CF}$ and $R_{CE}$, wherein $R_{CF}$ is the radius of curvature of that portion of the condyle which is weight bearing in flexion and $R_{CE}$ represents that portion of the curvature of the condyle which is weight bearing in extension, and (b) a medial lateral radius $R_{CML}$; and
   a second component, at least a portion of which is made of a plastic material and includes a pair of laterally spaced apart concavities, each of which is adapted to receive one of the condyles of the first component, the articulating surfaces of such concavities being defined by an anterior posterior radius $R_{TAP}$ and a medial lateral radius $R_{TML}$,
   wherein said condyles and concavities are formed such that the ratio $R_{CML}/R_{TML}$ is about 0.96 and the ratio $R_{CE}/R_{TAP}$ is between 0.60 and 0.75.

2. A joint prosthesis according to claim 1, wherein said condyles and concavities are formed such that the ratio $R_{CF}/R_{TAP}$ is between 0.4 and 0.5.

3. A joint prosthesis comprising:
   a femoral component which includes a pair of laterally spaced apart condyles each of which is cured generally to be similar to the shape of an anatomical femoral condyle, the surface of each said condyle being defined at least in part by (a) anterior posterior radii $R_{CF}$ and $R_{CE}$, wherein $R_{CF}$ is the radius of curvature of that portion of the condyle which is weight bearing in flexion and $R_{CE}$ represents that portion of the curvature of the condyle which is weight bearing in extension, and (b) a medial lateral radius $R_{CML}$; and
   a tibial component, at least the upper portion of which is made of a plastic material and includes a pair of laterally spaced apart concavities, each of which is adapted to receive one of the condyles of the femoral component, the surfaces of such concavities being defined by an anterior posterior radius $R_{TAP}$ and a medial lateral radius $R_{TML}$, wherein said condyles and concavities are formed such that the ratio $R_{CML}/R_{TML}$ is about 0.96 and the ratio of $R_{CF}/R_{TAP}$ is between 0.60 and 0.075.

4. A knee joint prosthesis according to claim 3, wherein said condyles and concavities are formed such that the ratio $R_{CF}/R_{TAP}$ is between 0.4 and 0.5.

5. A knee joint prosthesis according to claim 3, wherein said tibial component includes an upwardly extending post having a posterior concavely curved cam portion, and wherein said femoral component includes a cam follower portion adapted to engage said cam portion to provide posterior stabilization, the cam follower and cam surfaces being arranged such that they engage each other when the knee is flexed about 70–80 degrees.

* * * * *